United States Patent
Li et al.

(10) Patent No.: US 7,473,341 B2
(45) Date of Patent: *Jan. 6, 2009

(54) DENATURANT-FREE ELECTROPHORESIS OF BIOLOGICAL MOLECULES UNDER HIGH TEMPERATURE CONDITIONS

(75) Inventors: Qingbo Li, State College, PA (US); Kevin J. Levan, State College, PA (US); Heidi Monroe, Pittsburgh, PA (US)

(73) Assignee: Applera Corporation, Foster City, CA (US)

( * ) Notice: Subject to any disclaimer, the term of this patent is extended or adjusted under 35 U.S.C. 154(b) by 591 days.

This patent is subject to a terminal disclaimer.

(21) Appl. No.: 10/661,558

(22) Filed: Sep. 15, 2003
(Under 37 CFR 1.47)

(65) Prior Publication Data
US 2004/0256229 A1  Dec. 23, 2004

Related U.S. Application Data

(63) Continuation of application No. 10/258,547, filed as application No. PCT/US01/13336 on Apr. 25, 2001, now abandoned.

(60) Provisional application No. 60/199,389, filed on Apr. 25, 2000.

(51) Int. Cl.
*G01N 27/447* (2006.01)

(52) U.S. Cl. .................................... 204/455; 204/469
(58) Field of Classification Search .................. 204/455, 204/469, 605, 621, 451, 457, 601, 616
See application file for complete search history.

(56) References Cited

U.S. PATENT DOCUMENTS

| 4,254,249 | A | * | 3/1981 | Cottrell et al. ............. 525/329.4 |
|---|---|---|---|---|
| 4,906,344 | A | * | 3/1990 | Hjerten ......................... 204/451 |
| 5,264,101 | A | * | 11/1993 | Demorest et al. ............. 204/452 |
| 5,290,418 | A | * | 3/1994 | Menchen et al. ............. 204/455 |
| 5,409,586 | A | * | 4/1995 | Kamahori et al. ............. 204/452 |
| 5,458,761 | A | | 10/1995 | Kamahori et al. |
| 5,582,705 | A | * | 12/1996 | Yeung et al. ................. 204/603 |
| 5,633,129 | A | | 5/1997 | Karger et al. |
| 5,795,720 | A | * | 8/1998 | Henco et al. .................... 435/6 |
| 5,885,432 | A | * | 3/1999 | Hooper et al. ................ 204/469 |
| 6,214,187 | B1 | | 4/2001 | Hammond et al. |
| 6,770,698 | B1 | * | 8/2004 | Chu et al. .................... 524/458 |
| 6,926,815 | B2 | * | 8/2005 | Liu et al. ..................... 204/455 |
| 7,175,750 | B2 | * | 2/2007 | Guo et al. .................... 205/451 |
| 2003/0039996 | A1 | * | 2/2003 | Dunlop et al. .................. 435/6 |

* cited by examiner

*Primary Examiner*—Kaj K Olsen

(57) ABSTRACT

The present invention relates to a method of separating a sample comprising biological compounds, such as nucleic acids. The nucleic acids are subjected to electrophoresis using a matrix that is essentially free of denaturants and having at least one random, linear copolymer comprising a first comonomer of acrylamide and at least one secondary comonomer. A temperature of at least a portion of the matrix is at least about 80° C.

19 Claims, 9 Drawing Sheets

DENATURANT-FREE ELECTROPHORESIS OF BIOLOGICAL MOLECULES UNDER HIGH TEMPERATURE CONDITIONS

RELATED APPLICATIONS

The present application is a Continuation of U.S. patent application Ser. No. 10/258,547, filed Oct. 25, 2002, now abandoned which is the national phase application of PCT/US01/13336, filed Apr. 25, 2001, which claims priority to U.S. Provisional Application No. 60/199,389, filed Apr. 25, 2000, which applications are incorporated herein.

FIELD OF THE INVENTION

The present invention relates to methods and devices for sequencing nucleic acids in separation matrices that are essentially free of chemical denaturants.

BACKGROUND

A conventional DNA sequencing gel matrix typically contains 3-9 M urea, or a combination of urea and formamide as a denaturant. The function of a denaturant in a gel is to help keep DNA molecules denatured during electrophoresis in order to achieve accurate base calling. The existence of urea or formamide in a gel matrix represents a distinctive difference between denaturing gel electrophoresis for DNA sequencing (separating single-stranded DNA) and non-denaturing gel electrophoresis for separating double stranded DNA. The denaturing power of a gel matrix is generally proportional to the concentration of a denaturant in the gel matrix. Higher denaturing powers minimize compression, a self-folding behavior, of single stranded DNA fragments in a DNA sequencing sample.

When urea is used, however, the denaturing power is limited by the saturation concentration of urea, which is about 9M. When formamide is used, there is also a limit, which is the manageable viscosity of a matrix and separation speed. For example, because the viscosity of the matrix increases significantly with the percentage of formamide in a gel, separation speed decreases with higher percentages of formamide. Sometimes, the denaturing power of a gel with a maximum concentration of urea or formamide still does not provide sufficient denaturing power to resolve some compression bands in GC-rich DNA samples.

A popular method to overcome the above-mentioned problem of insufficient denaturing power is to heat up a gel during electrophoresis, typically 35-70° C., and add a denaturant. The combination of high temperature electrophoresis and high concentration denaturant typically provides sufficient denaturing power to resolve difficult compression bands.

There are several issues, however, associated with electrophoresis using a matrix containing urea or formamide. First, urea and formamide degrade in the basic solution that is typically used for DNA sequencing (pH 8.0-8.5). Higher temperatures accelerate such degradation. The degradation of urea or formamide has adverse effects on the gel and separation columns. The degradation products include ammonia, uric acid, and formic acid. These products increase the ion concentration and pH of the matrix. They may also cause bubble formation in a matrix at higher temperatures. When an uncoated capillary is used, these degradation products reduce the adhering affinity between the polymer dynamic coating and the capillary wall. This allows electroosmotic flow to occur, which consequently reduces separation efficiency. Capillary lifetime is also shortened because the decreased coverage of polymer coating on the capillary wall allows biomolecules to attack and adsorb onto the capillary wall, which in turn degrades separation efficiency.

To minimize these problems, one can take several approaches: a) optimize the electric field strength and column temperature so that the degradation products can be consistently driven out of the separation column at a rate that is equivalent to or higher than the rate of generation; b) develop better dynamic coating polymers that adsorb onto capillary wall more efficiently under high temperature; c) reduce the pH value of the gel matrix, e.g., from pH 8.3 down to pH 7.6, in order to reduce the degradation rate of urea or formamide at high temperatures, and to enhance the adsorbing efficiency of polymer on the capillary wall. These methods, however, have limitations.

SUMMARY OF THE INVENTION

The present invention relates to a method of separating a mixture of nucleic acids, comprising subjecting the biological molecules to electrophoresis using a matrix that is essentially free of denaturants, the matrix having at least one random, linear copolymer comprising a first comonomer of acrylamide and at least one secondary comonomer, wherein a temperature of at least a portion of the polymer matrix is at least about 75° C., and more preferably at least about 80° C. The maximum temperature of the matrix should be less than the boiling point of a fluid within the matrix, but preferably is less than about 95° C. In one embodiment, the matrix is completely free of denaturants.

The comonomers are preferably randomly distributed along the copolymer. At least one secondary comonomer is selected from the group consisting of vinyl monomers, monomers of acrylamide derivatives, monomers of acryloyl derivatives, monomers of acrylic acid derivatives, monomers of polyoxides, monomers of polysilanes, monomers of polyethers, monomers of derivatized polyethylene glycols, monomers of cellulose compounds, or mixtures thereof, each having between 2-24 carbon atoms.

In one embodiment, the copolymer is polymerized using about a 1:1 ratio of acrylamide and another comonomer. The other comonomer is preferably N,N-dimethylacrylamide monomer. The ratio of reactivity of the at least one secondary comonomer to said primary comonomer is preferably between 0.3 and 2.

In another embodiment, the matrix has a viscosity between 100 and 50,000 Cp. The at least one linear random copolymer has a molecular weight between 100,000 and 5,000,000 Daltons. In a preferred embodiment the copolymer comprises a buffer having a basic pH. Preferably, the buffer comprises about 89 mM Tris, 89 mM borate, and 2 mM EDTA. In a preferred embodiment, the buffer has a pH of at least about 8 and preferably from about pH 8 to pH 8.3.

In yet another embodiment, a second mixture of nucleic acids is subjected to electrophoresis within the matrix with at least a portion of the matrix being heated to at least about 75° C., preferably at least about 80° C. The second mixture of nucleic acids may be identical to the earlier electrophoresed mixture or the second mixture may be different. Preferably, the electrophoresis step can be repeated up to at least about 25 times so that about 25 mixtures can be electrophoresed without first providing a new matrix.

In another embodiment, a cooled portion of the matrix is cooled to less than about 25° C. The cooled portion is preferably disposed between a detection zone of the matrix and the heated portion of the matrix so that the cooled portion receives nucleic acids from the heated portion of the matrix.

The length and temperature of the cooled portion are preferably selected to allow DNA that was denatured in the heated portion to substantially re-anneal prior to being detected.

Another embodiment of the invention relates to a method of electrophoresing a plurality of mixtures of biological compounds, comprising subjecting a first mixture to electrophoresis using a matrix that is essentially free of denaturing agents, the first mixture comprising nucleic acids, and wherein a temperature of at least a portion of the matrix is sufficient to substantially denature the nucleic acids. During electrophoresis of the first mixture, the temperature of the matrix preferably is between 80° C.-99° C. More preferably, the temperature is between 80° C.-95° C. and most preferably is between 80° C.-90° C. The temperature of the matrix is insufficient to boil a fluid, such as water, present in the matrix and so this determines the upper temperature limit, subject to the atmospheric conditions.

A second mixture is subjected to electrophoresis using substantially the same matrix, the second mixture comprising a complex of at least two biological compounds. By substantially the same matrix it is meant, for example, that the same support is used to electrophorese both the first and second mixtures without first replacing more than about 20% of the matrix present in the support. Preferably, less than about 5%, and more preferably none of the matrix is replaced. In a preferred embodiment, the complex comprises at least one of a nucleic acid-protein complex and a protein-protein complex. It should be understood that the first and second mixtures can be electrophoresed in either order.

Another embodiment of the present invention relates to a system for electrophoretically sequencing at least one nucleic acid sample. The system comprises at least one support suitable for retaining a matrix in which electrophoretic separation of nucleic acid samples may be conducted. A heat source is in thermal contact with the at least one support, the heat source being configured to heat at least a portion of the at least one support to at least about 80° C. The support preferably provides sufficient thermal contact between the heat source and the matrix retained by the support so that heating the support to at least about 80° C. also heats a portion of the matrix to at least about 80° C.

In one embodiment, the system further comprises a cooling device configured and arranged to cool a cooled portion of the at least one support, the cooled portion receiving samples from the heated portion of the support and being disposed between the heated portion and a detection zone of the capillary. The cooling device is preferably configured to cool the temperature of the cooled portion of the capillary to less than about 25° C.

In another embodiment, the support contains a matrix suitable for electrophoretic separation of a nucleic acid sample, the matrix being essentially free of denaturing agents.

Another embodiment of the present invention relates to a system for electrophoretically sequencing a plurality of nucleic acid samples, the system comprising a plurality of capillaries, each capillary having a first end, the first ends being arranged in a two-dimensional array corresponding to an array of wells of a microtitre tray, each of said wells configured to contain at least one of the nucleic acid samples. The system includes an apparatus to fluidly associate each of said nucleic acids samples with a respective first end to introduce the nucleic acid samples to the capillaries. Fluidly associating a sample with the first end of the capillary with a sample in a well preferably introduces a sufficient quantity of the sample into the capillary to allow electrophoretic separation of the nucleic acids in the sample followed by detection of the separated nucleic acids.

The device includes a heat source in thermal contact with said plurality of capillaries and configured to heat at least a heated portion of each of said capillaries to a temperature of at least about 80° C., and computer means configured to operate the heat source to heat the heated portions to at least about 80° C.

The system preferably includes a light source arranged to illuminate said samples and a detector arranged to detect fluoresced light emitted by said samples.

In one embodiment, the system further comprises a cooling device configured and arranged to cool a cooled portion of each of at least some of the capillaries, the cooled portions disposed to receive nucleic acids from the heated portions of the capillaries. The cooling device is preferably configured to cool a temperature of each cooled portion to less than about 25° C.

In another embodiment, the capillaries contain a matrix suitable for electrophoretic separation of a nucleic acid sample, the matrix being essentially free of denaturing agents.

BRIEF DESCRIPTION OF THE DRAWINGS

The present invention is described in detail below with reference to the drawings in which.

DETAILED DESCRIPTION OF THE INVENTION

Matrix for Electrophoresis

Figure 1A:
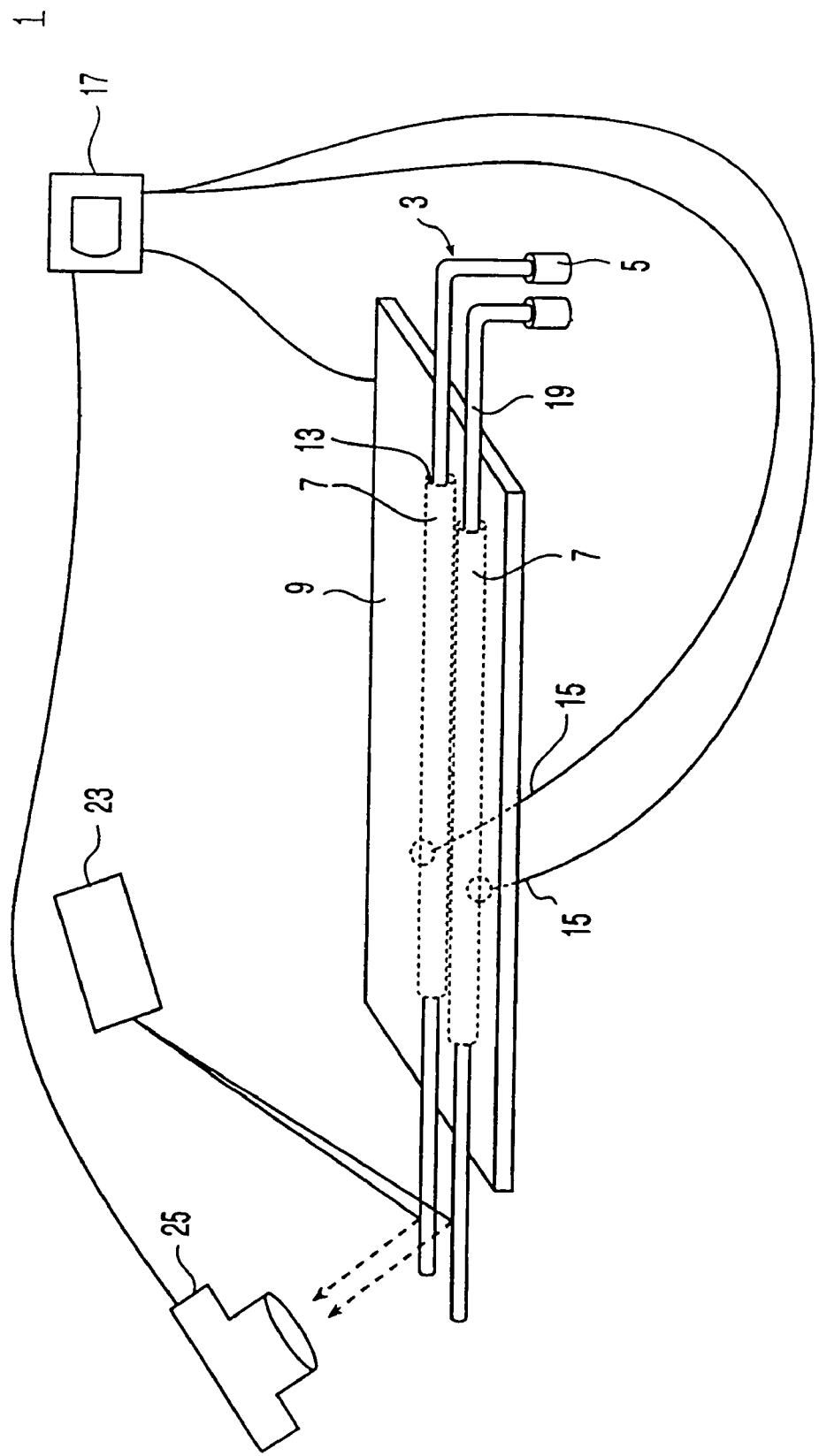
FIG. 1a & 1b show two embodiments for a device utilizing thermal denaturation in accordance with the present invention.

The present invention overcomes the problems associated with the presence of denaturing agents such as, for example, urea or formamide, in a medium configured to support the electrophoretic separation of biological molecules. Preferably, the medium is configured to support the electrophoretic sequencing of nucleic acids such as DNA under temperature conditions sufficient to at least partially denature the nucleic acids. The medium is preferably a matrix, such as a sieving matrix, that is essentially free of urea, formamide, or other denaturing agents. As used herein, the term matrix is synonymous with the term gel, which is often used to describe media used for electrophoretic separations.

The matrix of the present invention may be used with any suitable electrophoresis format, such as, for example, slab gel electrophoresis, capillary electrophoresis, or microchip electrophoresis. Preferably, the matrix is retained by a support that, together with the matrix, defines a path through which a sample migrates. Suitable supports include, for example, plates for retaining slab gels, a capillary, or microchip channel. The support is preferably coated or otherwise modified to minimize electroosmotic flow, as understood in the art. Modified supports include supports that are formed materials, such as plastics or other polymers, that themselves minimize electroosmotic flow. Alternatively, the matrix itself can provide a "coating" function reducing the amount of electroosmotic flow. It should be understood, however, that the present invention is suitable for use with supports that are either unmodified or uncoated such that electroosmotic flow occurs.

By essentially free of denaturing agents it is meant that denaturing agents, if any, are present in the matrix in an amount such that the agents themselves or degradation products of the agents do not adversely affect the matrix or separation support. For example, separation supports are typically modified or configured to minimize electroosmotic flow during sequencing. The denaturing agents, if present, are preferably present in an amount that is insufficient to increase electroosmotic flow by an amount sufficient to degrade separation performance. More preferably, the essentially denaturant free matrix of the present invention is completely free of urea, formamide, and other denaturing agents.

Because the denaturing power of the present matrix preferably depends upon the temperature of the matrix, rather than the presence of a denaturing agent, the same matrix can be operated in denaturing mode for one sample and in non-denaturing mode for a successive sample. The ability to alternate the same matrix between denaturing and non-denaturing modes advantageously increases the rate at which successive samples can be analyzed because time consuming capillary flushing steps are not required to remove or add the denaturing agent to the matrix or to change the matrix itself. For example, the matrix of the present invention may be used to separate a first sample of double-stranded DNA, without thermal denaturing, and to separate a second sample of DNA in the form of single-stranded DNA using thermal denaturing, as in DNA sequencing.

The matrix of the present invention also allows binding assays to be performed in the same matrix that can be used for sequencing DNA with denaturing. For example, electrophoretic assays of DNA-protein interactions or assays of protein-protein interactions require that the temperature of the matrix be raised sufficiently high to induce electrophoretic mobility differences in the DNA-protein or protein-protein complex. The present matrix, being essentially free of denaturing agents, allows the same matrix to be operated at temperatures sufficiently high to perform a binding assay on one mixture and sequence DNA with thermal denaturing in a second mixture. Of course, by reducing the temperature, the same matrix can be used to separate mixtures without denaturing. As used herein, the term mixture refers to a sample comprising compounds to be separated, sequenced, or otherwise assayed to determine a property of a compound present in the sample. Assays include both qualitative and quantitative determinations.

The matrix of the present invention can also be used in the quantitation or quality control of products formed during a polymerase chain reaction (PCR). The PCR products can be very large, such as greater than about 1000 basepairs. The matrix of the present invention can be operated with a viscosity sufficiently low to facilitate separation of the large PCR products.

In order to compensate for the loss of denaturing power due to being essentially free of denaturants, the temperature of at least a heated portion of the matrix is preferably sufficient to denature substantially all of the DNA to be sequenced. The heated portion preferably comprises substantially all of the migration distance, which is the distance along the migration path between the region where the mixture is introduced into the matrix and the region where components of the mixture are detected. For example, the heated portion of the matrix comprises at least 50%, preferably at least 75%, more preferably at least 85%, of the migration distance. Thus, during electrophoresis, DNA in a mixture preferably remains denatured for substantially all of the migration time. Preferably, the DNA remains denatured for at least 50%, of the time required to migrate from the injection region to the detection region.

The temperature of the heated portion is at least about 75° C., and preferably is between 80° C.-99° C. More preferably, the temperature is between 80° C.-95° C. and most preferably is between 80° C.-90° C.

The polymer of the matrix of the present invention may be any polymer that is suitable for use in electrophoresis and is able to be operated at temperatures sufficient to denature at least a portion of the DNA. Preferably, the polymer is a copolymer formed of a 1:1 ratio of acrylamide and N, N-dimethylacrylamide (DMA) monomer. The matrix of the present invention preferably contains from about 0.2 to about 10% copolymer by weight. More preferably, the amount of copolymer is from about 1 to 6%, with about 5% most preferred. Polymerization techniques suitable to produce polymers of the present invention and other polymers suitable for use in the present invention, are described in international application no. PCT/US00/00793 published Jul. 20, 2000 as publication number WO 0042423, which is incorporated herein by reference in its entirety.

In a preferred embodiment, the matrix comprises at least one random copolymer forming a targeted linear copolymer. The random copolymer preferably includes more than one monomer, with different monomer units being distributed along the copolymer chain in no specific pattern. Preferably, the copolymer is not crosslinked with other copolymers. The random copolymers are preferably composed of at least two or more comonomer types. The ratio of comonomers can be continuously adjusted to optimize the properties for electrophoretic separation. The ratio of comonomers may be any ratio that provides the desired properties of the random copolymer. The comonomers must be sufficiently water soluble to be used in an electrophoretic separation. Typically, there is a primary comonomer that gives the random copolymer chain its primary physical, chemical, and sieving properties. Preferably, the primary comonomer is an acrylamide or an acrylamide derivative, which contains between 3-24 carbon atoms, is either saturated or unsaturated, and is either substituted or unsubstituted. Examples of suitable acrylamide derivatives include, but are not limited to, N,N-dimethacrylamide, N,N-dimethylmethacrylamide, N-ethylmethacrylamide, N-ethylacrylamide, N-methylacrylamide, N-methylmethacrylamide, and methacrylamide. The primary comonomers are available commercially or by simple derivatization of monomer units.

The secondary comonomers are selected for their inherent properties that may be incorporated into the copolymer chains. These inherent properties include, but are not limited to, one or more of hydrophilicity, hydrophobicity, self coating properties, copolymer chain backbone stiffness, stability of copolymer entanglement structure at different temperature and electric fields, resistance to hydrolysis, processivity of copolymer chain extension, gel matrix viscosity, affinity of the copolymer to the surface of a suitable supporting substrate, such as a coating layer on the inner surface or exposed bare surface of a capillary tubing, and chirality. The preferred inherent properties of the secondary comonomers are hydrophilicity, hydrophobicity, viscosity, and self coating properties. The selection of the secondary comonomers and the ratio of secondary comonomers to primary comonomer are based on predetermined desired properties of the targeted random comonomer.

At least one secondary comonomer may be copolymerized with the primary comonomer to form a random copolymer, wherein each comonomer unit is distributed along the copolymer chain in no specific order, and the ratio of the reactivity of the primary comonomer to the secondary comonomers is between about 0.3 to about 2. The reactivity is the probability that a given monomer is added to a growing copolymer chain in the presence of other types of monomers. Formation of the random copolymers is not limited to the copolymerization of one secondary comonomer with the primary comonomer. More than one secondary comonomer may be present in the formation of the random copolymers.

In another embodiment, the secondary comonomer or comonomers are vinyl monomers, monomers of acrylamide derivatives, monomers of acryloyl derivatives, monomers of acrylic acid derivatives and mixtures thereof. Preferably, the secondary comonomers are vinyl monomers, monomers of acrylamide derivatives, monomers of acryloyl derivatives, monomers of acrylic acid derivatives, monomers of polyoxides, monomers of polysilanes, monomers of polyethers, monomers of derivatized polyethylene glycols, monomers of cellulose compounds, and mixtures thereof, each having between 2-24 carbon atoms, is saturated or unsaturated, and is substituted or unsubstituted.

More preferably, the secondary comonomer includes at least one of methacrylamide, N-acryloylmorpholine, N-allylacrylamide, N-allylmethacrylamide, N, benzylacrylamide, N-benzylmethacrylamide, N-(iso-butoxymethyl)acrylamide, N-(iso-butoxymethyl) methacrylamide, N-(tert-butyl) acrylamide, N-tert-butyl)methacrylamide, N-cyclohexylacrylamide, N-cyclohexylmethacrylamide, N,N-diethylacrylamide, N,N-diethylmethacrylamide, N-[2-(N,N-dimethylamino)ethyl]acrylamide, N-[2-(N,N-dimethylamino)ethyl]methacrylamide, N-[3-(N,N-dimethylamino)propyl]acrylamide, N-[3-(N,N-dimethylamino)propyl]methacrylamide, N,N-dimethylacrylamide, N-methylmethacrylamide, N-methylacrylamide, N-ethylacrylamide, N-ethylmethacrylamide, N-phenylacrylamide, N-phenylmethacrylamide, N, N-diphenylacrylamide, N, N-diphenylmethacrylamide, N,N-dodecamethylenebisacrylamide, N-dodecylacrylamide, N-dodecylmethacrylamide, N-(2-hydroxypropyl)acrylamide, N-(2-hydroxypropyl)methacrylamide, N,N-methylenebismethacrylamide, N-methylolacrylamide, N-methylolmethacrylamide, N-propylacrylamide, N-propylmethacrylamide, N-isopropylacrylamide, N-isopropylmethacrylamide, N-butylacrylamide, N-butylmethacrylamide, N-isobutylacrylamide, N-isobutylmethacrylamide, vinyl acetate, vinylacetic acid, vinylbenzyl alcohol, vinylcyclohexane, N-vinyl formamide, 1-vinyl-2-pyrrolidinone, vinyl acetonitrile, vinyl acrylate, vinyl 4-tert-butylbenzoate, N-vinylcaprolactam, vinyl crotonate, vinylcyclopentane, vinyl decanoate, vinyl carbonate, vinyl 2-ethylhexanoate, 1-vinylimidazole, vinyl methacrylate, 2-vinylnaphthalene, 2-vinylpyridine, 4-vinylpyridine, vinyl sulfone, ethylene glycol vinyl ether, 1,6-hexanediol vinyl ether, N-vinylphthalimide, vinyl pivalate, 1-vinyl-2-pyrrolidinone, vinyl trifluoroacetate, 4,4'-vinylidenebis(N,N-dimethylaniline), or mixtures thereof. In another embodiment, the secondary comonomer can also include acrylamide alone or in combination with any of the above comonomers.

The random copolymers are synthesized by copolymerization of comonomers using methodology well known to those of ordinary skill in the art. The preferred method of copolymer synthesis is free-radical solution polymerization. Any free radical initiator well known to those of ordinary skill in the art may be used, including, but not limited to, peroxy compounds, azoalkanes, photochemical homolysis, biradicals, tin hydrides, alkyl amines, and heat. Preferably, the free radical initiator is a peroxy compound, an azoalkane, or alkylamine.

Typical polymerization initiators known to those of ordinary skill in the art can be used in the present invention. For instance, these initiators may be capable of generating free radicals. Suitable polymerization initiators include both thermal and photoinitiators. Suitable thermal initiators include, but are not limited to, ammonium persulfate/tetramethylethylene diamine, 2,2'-azobis-(2-amidino propane) hydrochloride, potassium persulfate/dimethylaminopropionitrile, 2,2'-azobis(isobutyro-nitrile), 4,4'-azobis-(4-cyanovaleric acid), and benzoyl-peroxide. Preferred thermal initiators are ammonium persulfate/tetramethyethylenediamine and 2,2'-azobisisobutyronitrile ("AIBN"). Suitable photoinitiators include, but are not limited to, isopropylthioxantone, 2-(2'-hydroxy-5'-methylphenyl)benzotriazole, 2,2'-dihydroxy-4-methoxybenzophenone, and riboflavin. When using the combination of persulfate and tertiary amine, the persulfate is preferably added prior to the addition of the non-aqueous medium, since persulfate is much more soluble in water than in non-aqueous dispersing media. More preferably, the free radical initiator is N,N,N',N'-tetramethylethylene-diamine ("TEMED"), or AIBN.

The matrix of the present invention has a higher long-term storage chemical stability because the matrix is at least essentially free of denaturing agents and detrimental degradation products therefrom. The matrix of the present invention also has a higher thermal stability and can be operated at higher temperatures to improve denaturing efficiency than if denaturants were present in the matrix. Denaturing agents can be thermally unstable and produce degradation products detrimental to the performance of the separation support and matrix.

A matrix of the present invention, which is essentially free of denaturing agents preferably has a lower viscosity than a matrix utilizing chemical denaturation, such as formamide, to achieve the same level of denaturation. This advantage is due at least in part to the higher level of heating that can be obtained with the present matrices. The lower viscosity allows faster separation speeds than if denaturants were used.

Advantages provided by running the essentially denaturant free matrix of the present invention also include, for example, an increased capillary lifetime, a longer sequencing read length, and a higher confidence level of a called base, as measured by a phred score, which is described below. For example, when a 5% 1:1 copolymer matrix containing 7M urea is used for room temperature electrophoresis, a capillary array lasts only up to 14 runs. A capillary comprising the essentially denaturant free matrix of the present invention lasts for more than about 25 runs. Thus, for example, at least about 25 samples can be run in sequence without providing a new matrix within the separation support. The actual number of runs that can be obtained with a single capillary before providing a new matrix depends, for example, upon the type of coating and the operating temperature.

The 5% 1:1 copolymer essentially denaturant free matrix running at 80° C. has a longer sequencing read length than the same matrix with urea running at about 20° C. This is an indication of the efficient denaturing power achieved by running the matrix at 80° C. This is further validated by sequencing PGEM/U using universal M13 reverse primer, which has been widely used as a control sample in commercial DNA sequencers. The PGEM/U sample running at 80° C. using the non-denaturant matrix shows no sign of compression, whereas the same sample run in a denaturing matrix does show signs of compression.

Without urea or formamide present in the matrix, the matrix is more stable at elevated temperature. Preferably the matrix can be heated to a temperature sufficiently greater than the reannealing temperature of the DNA to disrupt the secondary structure of the DNA, which improves read length. Because separation is faster at higher temperatures, one can lower the running voltage to further extend the read length. The matrix of the present invention provides a read length greater than about 600 base pairs and more preferably greater than about 650 base pairs.

A Phred score is a standard used widely in the sequencing community to measure the quality or confidence level of a called base. It is the negative logarithm of the error probability of a called base. For example, a Phred score of 20 for a base means the probability of error for calling this base is 1/100 or 1%. A Phred score of 20 is a standard cut-off threshold used in popular sequencing facilities. Only those bases with a Phred score greater than or equal to 20 are considered reliable and can be accepted into downstream in a sequence assembling process. As shown below, the present invention provides a higher phred score than achieved by using a sieving matrix comprising a denaturant such as urea.

Device for Separations Utilizing Thermal Denaturation

FIG. 1a shows a preferred arrangement of an embodiment of the present thermal sequencing device 1. A sample capillary 3 is provided to electrophoretically separate unknown sample compounds. As used herein, the term "capillary" collectively refers to any support or structure configured and arranged to separate a sample using electrophoresis. Thus, as used herein, the term "capillary" refers not only to what are commonly called capillaries but to microfabricated channels, and planar structures, such as used in slab gel electrophoresis. Capillary 3 is preferably arranged to be in fluid contact with a sample reservoir 5, which is configured to contain a volume of sample sufficient to perform an analysis. Examples of suitable sample reservoirs include the wells of a microtitre plate, a structure configured to perform PCR amplification on a volume of sample, a reservoir of a microfabricated electrophoresis device, and the like. Alternatively, where planar structures are used, an aliquot of sample can be added, such as by pipette, to the matrix.

Device 1 is provided with a power supply (not shown) suitable for providing a sufficient voltage and current for electrophoretic separation of a sample. The power supply is preferably configured to allow at least one of the current or resistance of the capillary to be monitored during a separation. Preferably, the current or resistance data is received by the computing device 17 to allow the electric potential to be varied to maintain a constant current or resistance.

A temperature controlled portion 7 of sample capillary 3 is arranged to be in thermal contact with a heat source such as a hot plate 9, or the like. Optionally, or in addition, the external heat source may comprise a wire, filament, or other heating element arranged external to the capillary. The capillary is preferably surrounded by a thermally conductive medium 13, to enhance thermal contact between the heating source and the capillary.

During electrophoresis, the external heat source, rather than ohmic heating of the separation medium itself, is preferably the dominant source of thermal energy to the separation medium within the capillary. The heat source is configured to heat the separation matrix to suitable operational temperatures of the matrix, as discussed above. The temperature is preferably sufficient to substantially denature DNA in the matrix without boiling a fluid in the matrix which is either essentially, or completely, free of denaturing agents. For example, the heat source is configured to heat the matrix to a temperature of at least about 75° C. and preferably between 80° C.-99° C. More preferably, the temperature is between 80° C.-95° C. and most preferably is between 80° C.-90° C.

The temperature of the capillary is monitored by a temperature sensing device in thermal contact with the separation support, such as a thermocouple 15, which preferably sends data to a computing device 17. The temperature measured by the temperature sensing device is considered to be the temperature of the separation matrix and the sample being electrophoresed. Hot plate 9 is preferably automatically controlled by computing device 17 in response to temperature data received from sensing device 15. Thus, device 1 preferably includes computer means comprising at least one of software or a memory configured to operate the heat source to heat the capillary to a temperature suitable for separation of thermally denatured nucleic acids, as described above.

Device 1 also includes a light source 23, such as a laser emitting light having a wavelength suitable to generate fluorescence from a fluorescent dye. A detector 25 is arranged to obtain fluorescence intensity data, such as a time-intensity electropherogram including peaks indicative of the presence of nucleotides, and send the detected fluorescence intensities to computing device 17. A detection system such as that disclosed in U.S. Pat. No. 6,118,127, can be used for this purpose.

In any embodiment of the present invention, the fluorescence intensity data of the unknown sample can be obtained simultaneously with the fluorescence intensity data of a second sample. By simultaneously, it is meant that the unknown and second samples are elecrophoresed in a total time at least about 25% less, preferably about 50% less, than twice the time required to sequentially electrophorese the samples. Preferably, the unknown sample is subjected to capillary electrophoresis in the sample capillary 3 and the second sample is simultaneously subjected to capillary electrophoresis in a second, different capillary 19.

Figure 1B:
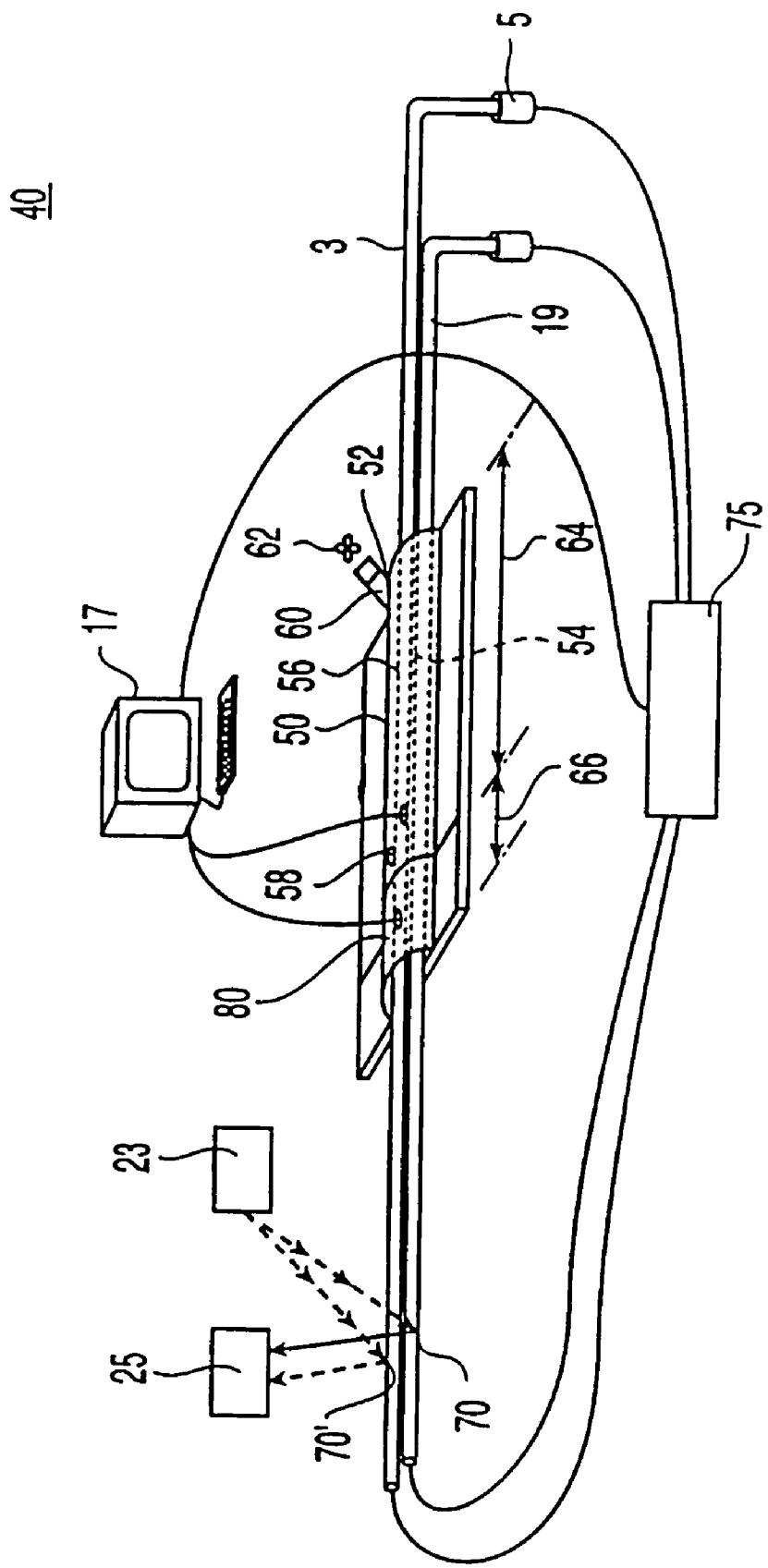

FIG. 1b shows another embodiment of a thermal denaturation device 40 in which a temperature control zone 50 of the sample capillary 3 and optional reference capillary 19 are placed in thermal contact with a gas, such as air or nitrogen. Device 40 is provided with a power supply 75, having the same features as the power supply of device 1 discussed above. Temperature control zone 50 preferably extends for a heated length 64 of the capillaries. At least one inlet port 52 is provided to introduce the heated gas to a region 54 between the capillaries and a thermal jacket 56 and at least one outlet 58 is provided to allow the gas to exit. Thermal jacket 56 insulates temperature control zone 50 to reduce heat loss from the temperature control zone 50.

The gas can be heated using, for example, a resistively heated filament 60 or a heat exchanger. Preferably, a fan 62 or other device to force the gas into the inlet and out of the exit is provided. Use of a gas, which has a lower viscosity than other fluids such as liquids, allows the temperature of the capillary to be changed much more rapidly because the temperature of the gas can be changed using, for example, a heated filament much more rapidly than that of a more viscous liquid. It should be understood, however, that a liquid may be used to thermostat the temperature of the temperature control zone.

A cooled zone 80 having a second, cooled length 66 of capillaries 3 and 19 can be provided to deliberately reduce the temperature of the samples being separated after the samples have passed through the temperature control zone 50. In the context, 'deliberate cooling' means something other than simply allowing the matrix to cool by simply exposing the capillary, microchip or slab to room temperature. The temperature in cooled zone 80 can be controlled using chilled air or other fluid or liquid with an arrangement similar to that provided in the temperature control zone. Alternatively, a peltier cooler can be arranged in thermal contact with this portion of the capillary, to reduce the temperature. The temperature and length 66 of cooled zone 80 are preferably low enough and long enough, respectively, to allow a DNA fragment that was thermally denatured within temperature control zone 50 to anneal prior to being detected at a reference detection zone 70 or a sample detection zone 70'. Thus, the cooled zone is configured and disposed to receive compounds that have migrated electrophoretically through heated zone 50 of the capillary. The temperature is reduced to less than about 45° C., more preferably to less than about 30° C., and most preferably to less than about 20° C.

EXAMPLE

The invention is further illustrated through the following non-limiting example.

Figure 2A:
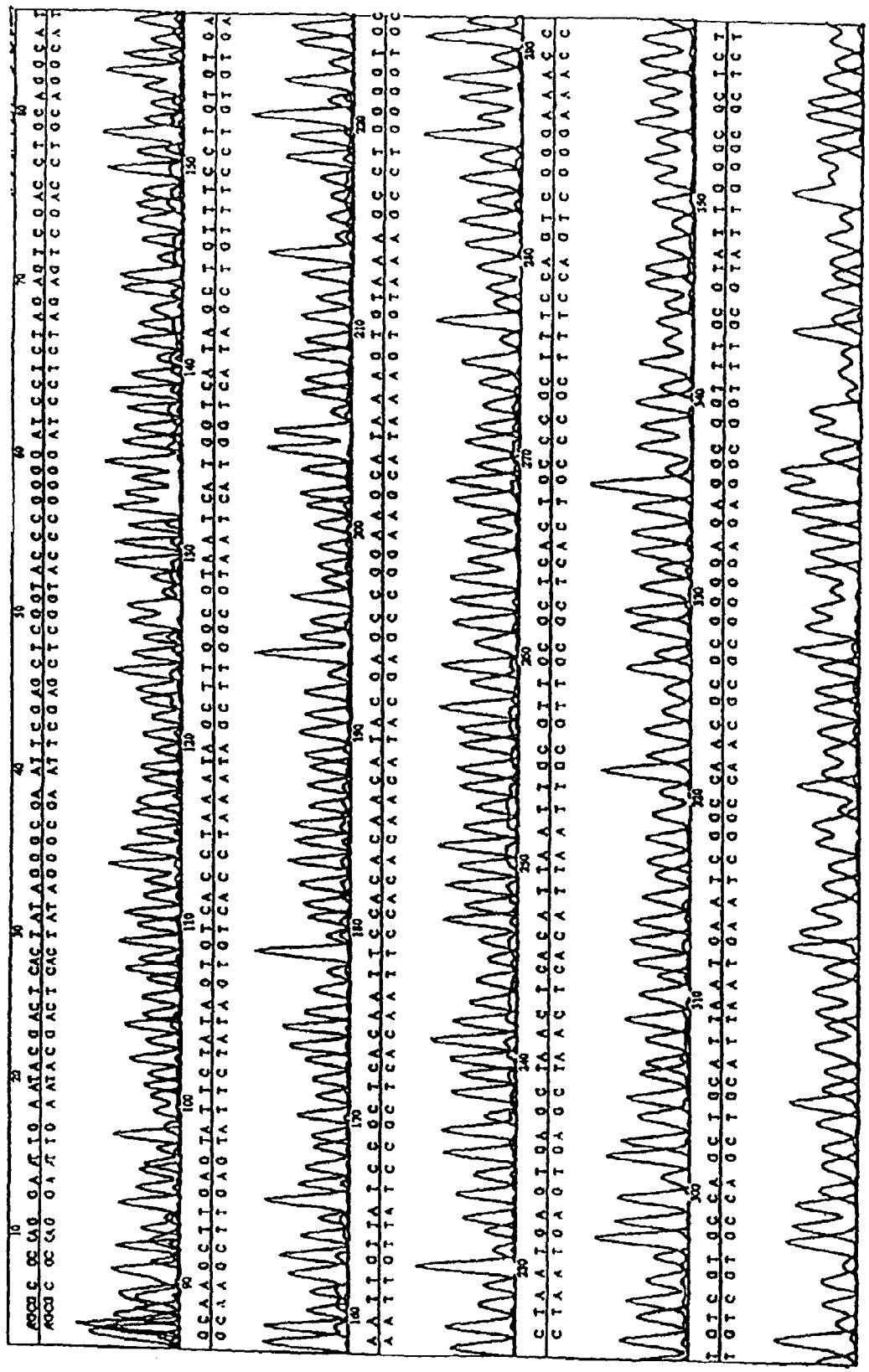
FIGS. 2a and 2b show the result of sequencing a PGEM/U sample using a 5% copolymer gel in 1×TBE, 7M urea, at room temperature.
Figure 2B:
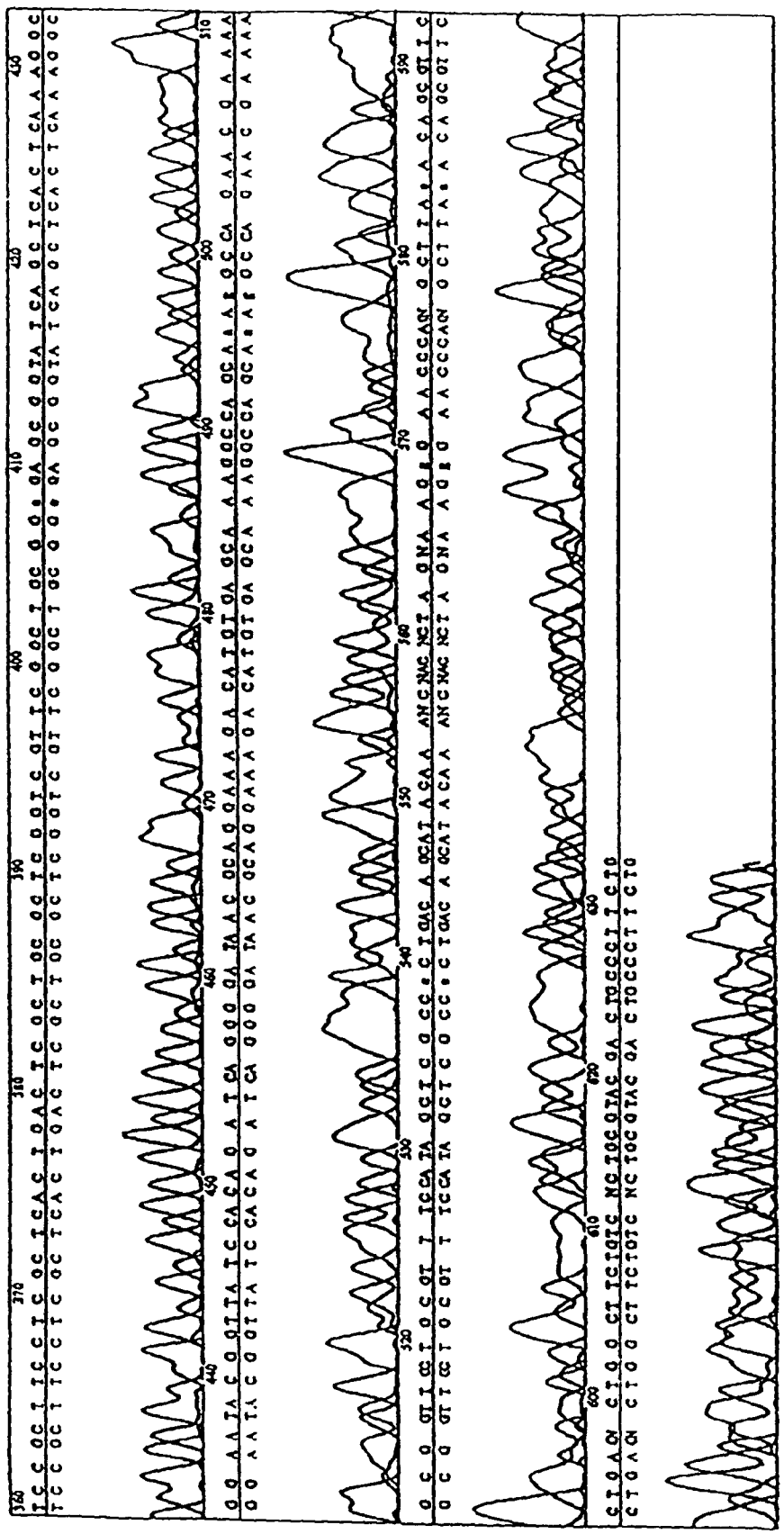

FIGS. 2a and 2b show the result of sequencing a PGEM/U sample using a 5% copolymer matrix in 1×TBE, 7M urea, at about 20° C. The copolymer was polymerized using a 1:1 ratio of acrylamide and N,N-dimethylacrylamide (DMA) monomer.

Figure 3:
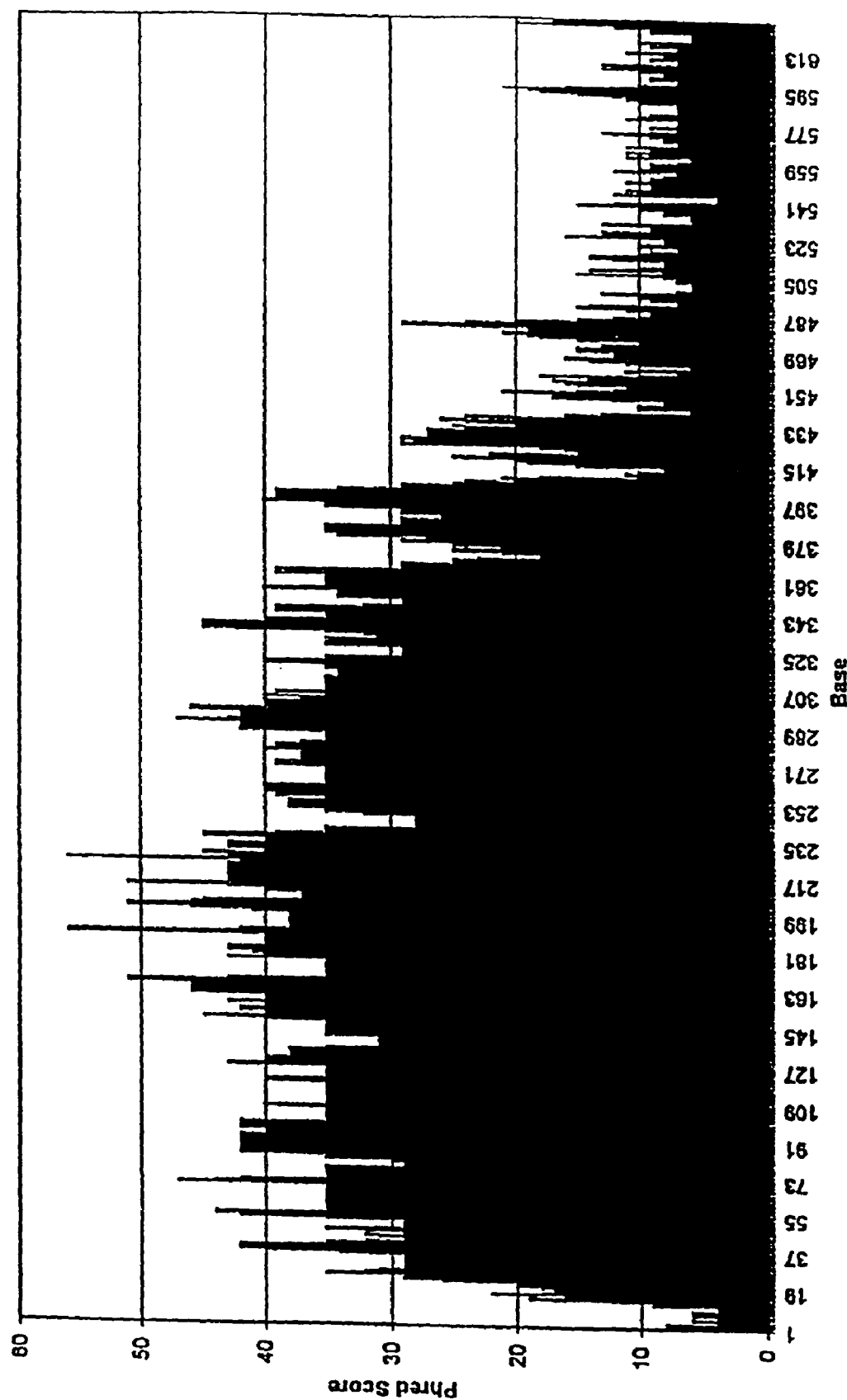
FIG. 3 shows a graph of Phred score versus called bases for the separation of FIGS. 2a and 2b.

As can be seen in FIG. 3, which shows the graph of Phred score versus called bases for FIGS. 2a and 2b, from base #25 to base #405, the called bases satisfy the criteria of Phred score 20. We define the section of the base sequence with Phred score greater than or equal to 20 as the trim length. For the example in FIG. 3, the trim length is 405−25=380. The trim length is used as a measurement of the matrix performance.

Figure 4A:
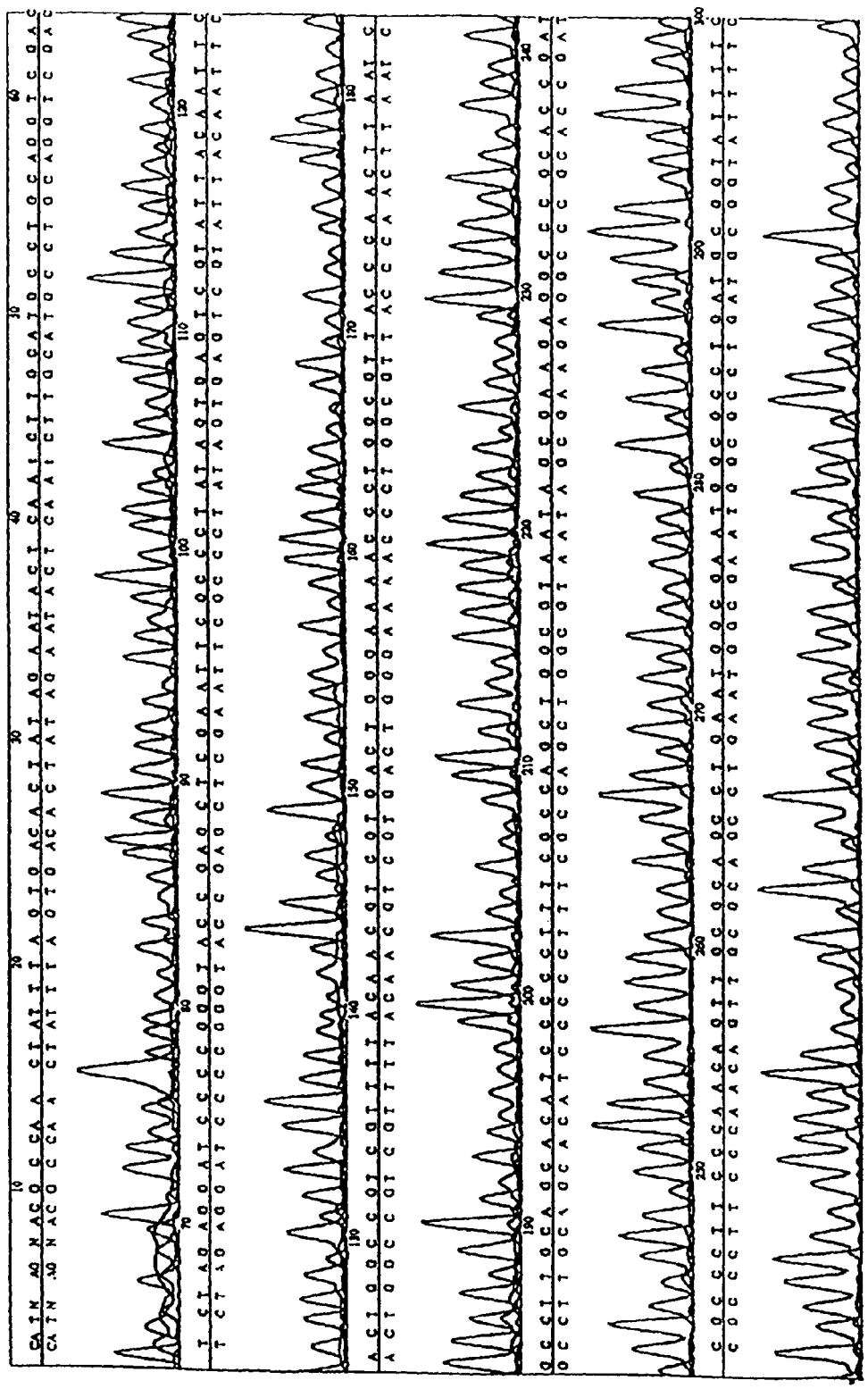
FIGS. 4a-4c show the result of sequencing a PGEM/U sample using 5% copolymer gel in 1×TBE with no urea, at 80° C. according to the present invention.
Figure 4B:
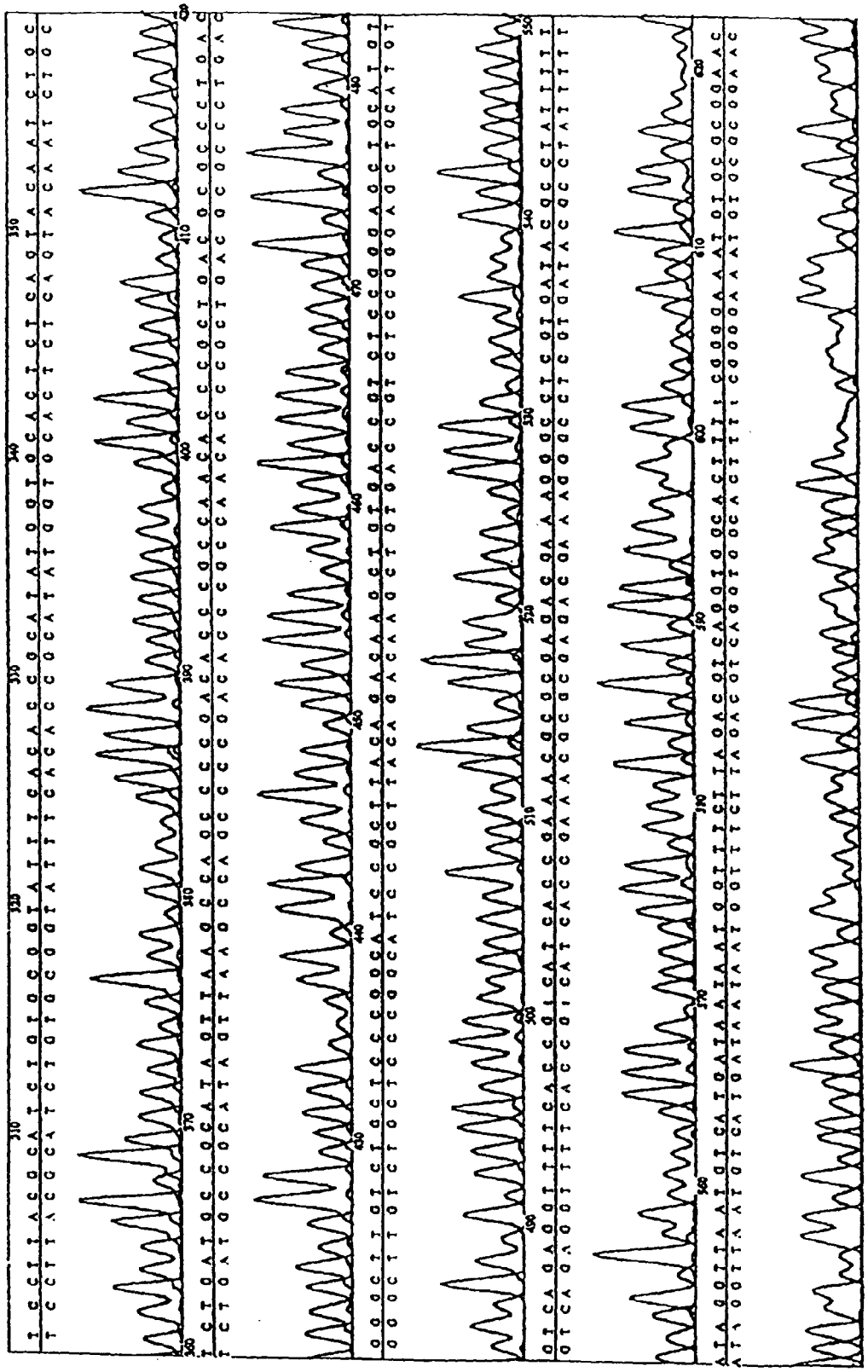
Figure 4C:
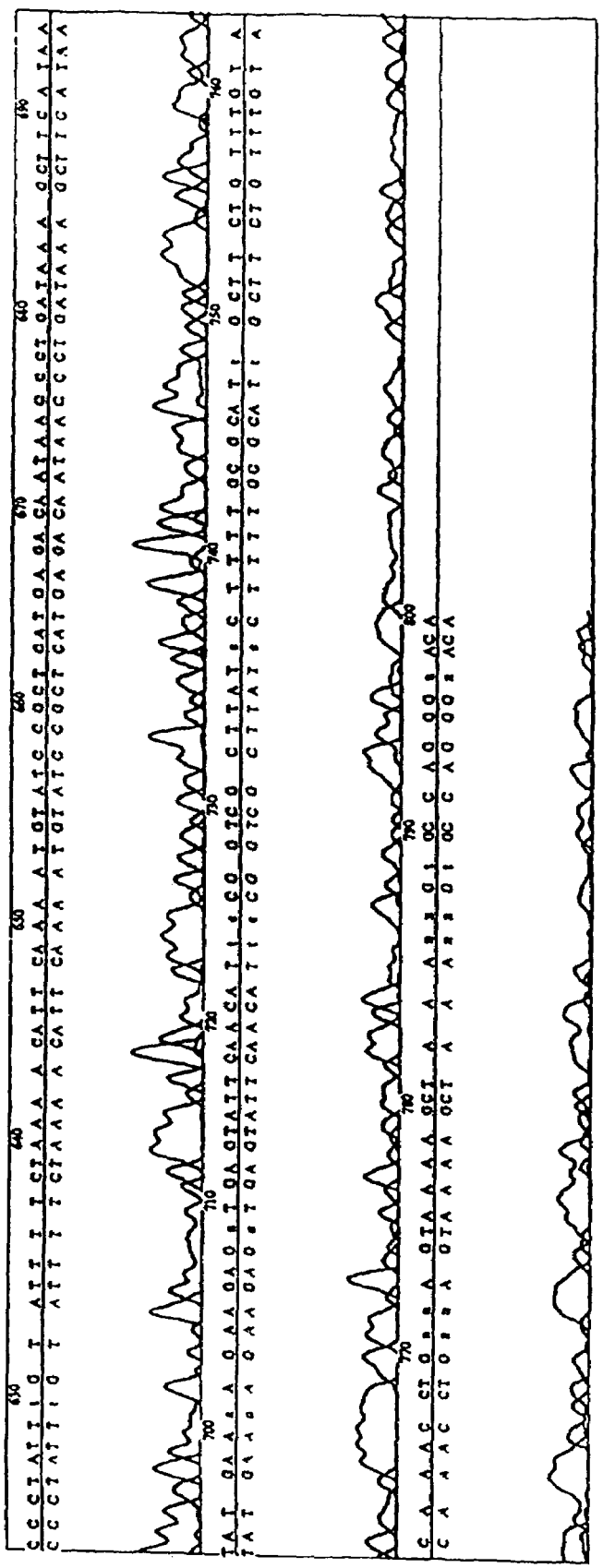
Figure 5:
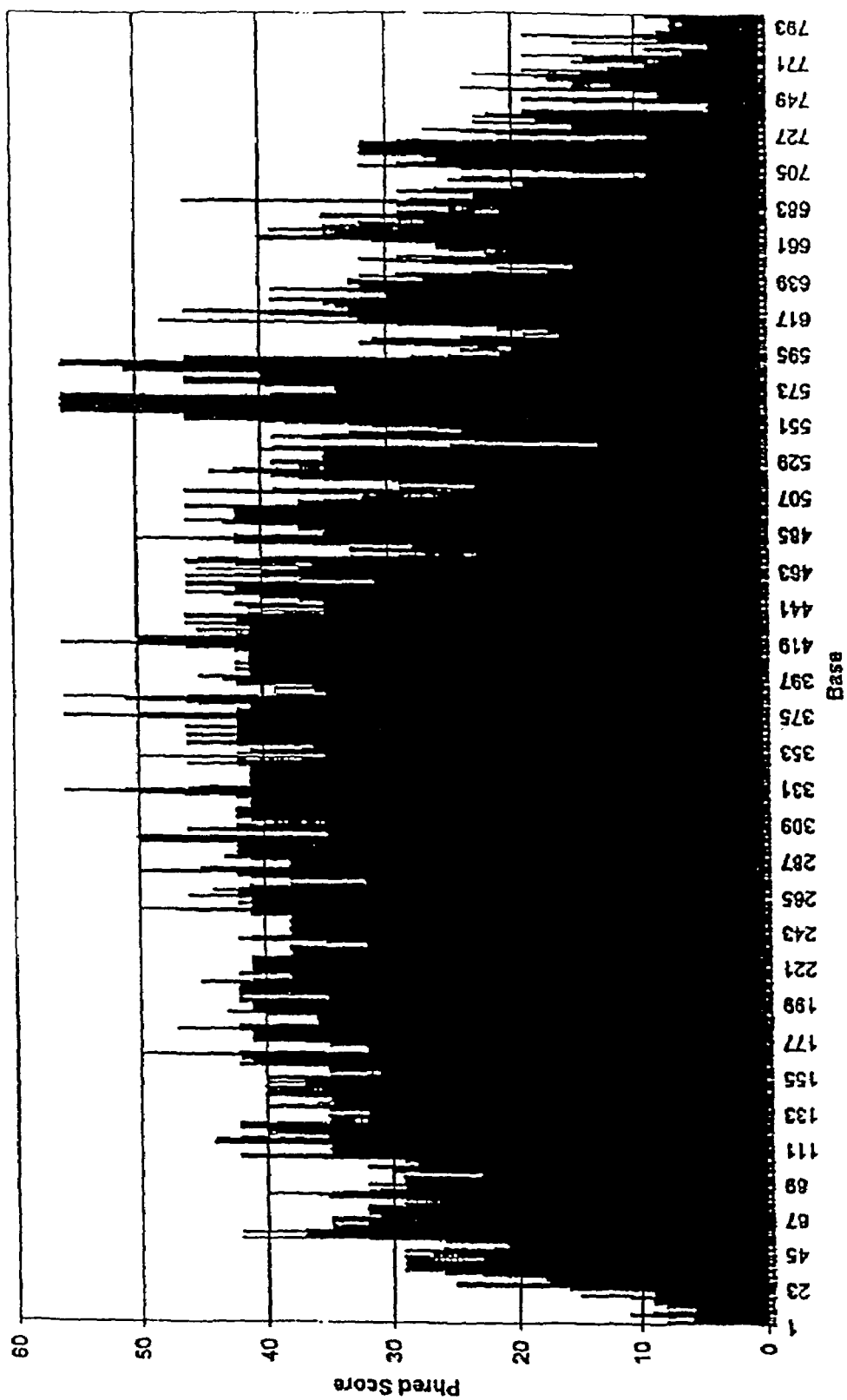
FIG. 5 shows the Phred score v. called bases for the separation of FIGS. 4a and 4b.

FIG. 4a and 4b show the result of sequencing a PGEM/U sample using 5% copolymer gel in 1×TBE, at 80° C. according to the present invention. No urea was used. The copolymer was polymerized from 1:1 acrylamide and DMA monomer. FIG. 5 shows the Phred score v. called bases. The trim length for this example is 720−34=686, which is an improvement over 380.

The present invention also provides a higher separation speed than electrophoresis using a chemical denaturant. For the example in FIGS. 2a and 2b using urea gel at room temperature, it takes 120 minutes for 500 bases to pass the detector. FIGS. 4a and 4b, however, show that using non-urea gel at 80° C. according to the invention, it takes 68 minutes for 500 bases to pass the detector, and 96 minutes for 800 bases to pass the detector. Overall, tremendous gain in separation speed and qualified sequencing length has been demonstrated by using the non-urea gel at 80° C.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed:

1. A method of separating nucleic acids, the method comprising:
   providing a matrix that is essentially free of denaturing agents, wherein the matrix has at least one random, linear copolymer comprising acrylamide and N,N-dimethylacrylamide;
   thermostatting a first portion of the matrix to at least about 80° C.; and
   subjecting the nucleic acids to electrophoresis through the first portion of the matrix that is thermostatted to at least about 80° C.

2. The method of claim 1, wherein the first portion of the matrix is thermostatted to a temperature between about 80° C. to about 90° C.

3. The method of claim 1, further comprising a second portion of the matrix, wherein the second portion of the matrix is thermostatted to less than about 30° C., and wherein the nucleic acids migrate through the second portion after they have first migrated through the first portion.

4. The method of claim 1, wherein the matrix is completely free of denaturing agents.

5. The method of claim 1, further comprising subjecting a second sample of nucleic acids to electrophoresis within the same matrix, after the first sample has been electrophoresed.

6. The method of claim 5, comprising subjecting a total of at least 25 additional samples of nucleic acids, one at a time, without replacing the matrix.

7. The method of claim 1, wherein the polymer is a copolymer polymerized using about a 1:1 ratio of acrylamide and N,N-dimethylacrylamide monomer.

8. The method of claim 1, further comprising:
   providing a detection portion of the matrix, wherein nucleic acids migrating from the first portion of the matrix are detected.

9. A method of sequencing a sample comprising nucleic acids, comprising:
   providing a matrix that is essentially free of denaturing agents, the matrix having at least one random, linear copolymer comprising about a 1:1 ratio of acrylamide and N,N-dimethylacrylamide monomer, and a buffer having a pH of at least about 8, a temperature of at least a portion of the matrix being at least about 80° C.;
   subjecting the nucleic acids to electrophoresis through said matrix; and
   prior to detecting the nucleic acids, thermostatting a second portion of the matrix to less than about 25° C., the second portion of the matrix receiving nucleic acids from the heated portion of the matrix.

10. The method of claim 9, further comprising:
    providing a detection portion of the matrix, wherein nucleic acids migrating from the second portion of the matrix are detected.

11. A method of separating a plurality of samples of biological compounds, comprising:
    providing a matrix that is essentially free of denaturing agents, wherein the matrix has at least one random, linear copolymer comprising acrylamide and N,N-dimethylacrylamide; and
    subjecting a sample to electrophoresis through said matrix, wherein a first portion of the matrix is thermostatted to a temperature of at least about 80° C.; and
    subjecting a sequence of samples to electrophoresis in separate steps through the same matrix.

12. The method of claim 11, wherein the temperature is from about 80° C. to about 99° C.

13. The method of claim 12, wherein the temperature is from about 80° C. to about 90° C.

14. The method of claim 12, further comprising thermostatting a second portion of the matrix to less than about 30° C., the first and second samples migrating through the second portion after each has first migrated through the first portion.

15. The method of claim 14, wherein the second portion of the matrix is thermostatted to less than about 25° C.

16. The method of claim 11, wherein the sample comprises at least one of nucleic acid, nucleic acid-protein complex and protein-protein complex.

17. The method of claim 11, further comprising:
providing a detection portion of the matrix, wherein samples migrating from the second portion of the matrix are detected.

18. The method of claim 11, wherein the sequence of samples is at least about 25 samples.

19. The method of claim 11, wherein the polymer is a copolymer polymerized using about a 1:1 ratio of acrylamide and N,N-dimethylacrylamide monomer.

* * * * *